United States Patent [19]

Boudakian

[11] 4,096,196

[45] Jun. 20, 1978

[54] DIAZOTIZATION-FLUORINATION IN A MEDIUM OF HYDROGEN FLUORIDE CONTAINING TERTIARY AMINE COMPOUNDS

[75] Inventor: Max M. Boudakian, Pittsford, N.Y.

[73] Assignee: Olin Corporation, New Haven, Conn.

[21] Appl. No.: 713,753

[22] Filed: Aug. 12, 1976

Related U.S. Application Data

[63] Continuation-in-part of Ser. No. 627,834, Oct. 31, 1975, abandoned.

[51] Int. Cl.$^2$ .................... C07D 213/02; C07C 25/13; C07D 213/04

[52] U.S. Cl. .......................... 260/650 F; 260/290 HL

[58] Field of Search ......... 260/290 HL, 649 F, 650 F

[56] References Cited

U.S. PATENT DOCUMENTS

| | | | |
|---|---|---|---|
| 3,471,512 | 10/1969 | Kollonitsch et al. | 260/309 |
| 3,573,214 | 3/1971 | Kollonitsch et al. | 252/182 |
| 3,798,228 | 3/1974 | Boudakian et al. | 260/290 HL |

OTHER PUBLICATIONS

Raphael et al., Advances in Organic Chemistry, Methods and Results, vol. 5, Interscience Pub., pp. 2, 3, 30 and 31, (1965).

Olah et al., J. Am. Chem. Soc., vol. 97, (1), Jan. 8, 1975.

*Primary Examiner*—Alan L. Rotman

*Attorney, Agent, or Firm*—William A. Simons; T. P. O'Day

[57] ABSTRACT

Process for preparing fluoroaromatic or fluoropyridines by diazotization-fluorination of aromatic or heterocyclic amines in a solution of hydrogen fluoride containing selected tertiary amine compounds.

24 Claims, No Drawings

DIAZOTIZATION-FLUORINATION IN A MEDIUM OF HYDROGEN FLUORIDE CONTAINING TERTIARY AMINE COMPOUNDS

CROSS-REFERENCE TO RELATED APPLICATIONS

This application is a continuation-in-part application of U.S. patent application Ser. No. 627,834, filed Oct. 31, 1975 now abandoned.

BACKGROUND OF THE INVENTION (1) Field of Invention

The present invention relates to an improved process for preparing fluoroaromatics or fluoropyridines by diazotization-fluorination of corresponding aromatic or heterocyclic amines in hydrogen fluoride. More particularly, the invention relates to processes in which a suitable amine substrate is diazotized with a diazotization reagent in hydrogen fluoride to form a corresponding diazonium fluoride and the diazonium fluoride is decomposed to form a corresponding aromatic or aromatic or heterocyclic fluoride. Specifically, the invention relates to an improved process in which the diazotization-fluorination is conducted in a solution of hydrogen fluoride containing selected tertiary amine compounds.

(2) Prior Art

Osswald et al, German Pat. No. 600,706 disclosed the conventional two-step process for diazotization-fluorination of primary aromatic amines utilizing sodium nitrate and anhydrous hydrogen fluoride. A solution was made of the amine in hydrogen fluoride and sodium nitrite was added, the temperature during addition being held below about 10° C until diazotization is complete. After completion of diazotization, the reaction mixture is refluxed (temperature 30° C-40° C) to decompose the diazonium fluoride, yielding nitrogen and the corresponding aromatic fluoride. Ferm and Vander Werf, J. Am. Chem. Soc., 72, 4809 (1950) expanded this technology to include other substrates. Shenk et al, U.S. Pat. No. 2,563,796 modified the process by utilizing gaseous nitrosyl chloride rather than sodium nitrite in order to obtain higher decomposition temperatures.

The Osswald et al and Ferm and Vander Werf teachings have been applied to numerous aromatic and heterocyclic amine substrates and their work-up procedures have been modified over the years to improve yields and facilitate product recovery.

Nevertheless, there is still a need for further improvement and efforts have been made to modify reaction conditions to obtain increased yields and/or further simplify the overall process. One such example is found in Misaki et al, Japanese Patent Publication 81330/74, published Aug. 6, 1974 pursuant to Japanese Application 126570/72, filed Dec. 15, 1972. In accordance with this teaching, improved yields were reportedly attained in a single step diazotization-decomposition by dissolving a diazotization agent, such as sodium nitrite, in excess anhydrous hydrogen fluoride (generating nitrous acid in HF), separately dissolving the diazotizable amine in hydrogen fluoride, then adding the diazotization compound in HF to the amine in HF at temperatures in the range of 30° C-50° C to simultaneously form and decompose the diazonium fluoride to the aromatic fluoride.

De Milt et al, J. Am. Chem. Soc. 58, 2044 (1936) disclosed that pyridine and certain other tertiary amines combined with an excess of strong mineral acid such as $H_2SO_4$ were good solvents for the diazotization of weakly basic and insoluble anilines. And, Spietschka, U.S. Pat. No. 3,888,841 disclosed this was also true in an alkaline environment in the presence of nitrosylsulfuric acid or nitrosyl chloride. Neither reference, however, teaches or suggests the use of tertiary amine compounds as described herein or the fluorination of amines utilizing hydrogen fluoride.

Boudakian et al, U.S. Pat. No. 3,798,228 discloses the preparation of difluoropyridine by tetrazotization-fluorination of suitable diaminopyridines with a diazotization reagent and hydrogen fluoride. Boudakian, U.S. Pat. No. 3,703,521 discloses the preparation of 4-fluoropyridine and its salts by this route utilizng a modified work-up procedure to stabilize the end product. Boudakian, German Offenlegungsschrift 2,113,253, discloses an integrated route to m-fluoroaniline by diazotization-fluorination of m-aminoacetanilides with sodium nitrite and hydrogen fluoride.

Kollonitsch, U.S. Pat. Nos. 3,471,511 and 3,573,214 and Kollonitsch et al., 3,471,512 discloses a process in which the diazotization-fluorination of aromatic amines is conducted in the absence of dimethylsulfoxide (DMSO) in HF. While the use of this mixture appears to have a beneficial effect on yields in many instances, this improvement is offset by high DMSO requirements and by severe corrosion which occurs in this media, making it commercially unattractive.

Research has also been carried out in the area of halogen exchange on aromatic or heterocyclic substrates. See Abramovitch, Pyridine and Its Derivatives, Supplement, Part Two, Vol. 14, pages 421-23 (1974) and Raphael et al, Advances in Organic Chemistry, Methods and Results, Vol. 5, pages 30 and 31, (1965). Here the halo groups on aromatic or heterocyclic substrates are exchanged for fluoro groups by the reaction with potassium fluoride. The chemistry is different than the present invention wherein both diazotization and fluorination is carried out in one medium of hydrogen fluoride containing selected tertiary amine compounds.

It has now been found that whether one employs the conventional two-step process or its modification or the one-step process, the presence of selected tertiary amine compounds in the hydrogen fluoride solution or medium, surprisingly and unexpectedly, enhances yields beyond those obtainable when diazotization is conducted in HF alone. It has also been found that the presence of tertiary amine compounds in HF will not result in equipment corrosion as has been found with DMSO. Further, it has been discovered that these compounds need only be used in low concentrations and that their presence simplifies product recovery by improving phasing of organic and inorganic layers. Moreover, the use of these compounds permits diazotization-fluorination in HF of substrates which previously with HF alone gave principally tars.

SUMMARY OF THE INVENTION

The present invention, therefore, comprises an improved process for diazotization-fluorination of aromatic or heteroaromatic amines in hydrogen fluoride wherein the diazotization and decomposition steps are conducted in the presence of a solution of hydrogen fluoride containing tertiary amine compounds.

In general, the present invention has the advantage of making the diazotization-fluorination process more commercially viable by increasing the yields of the products therein produced, facilitating the procedures employed to carry out the process, and broadening the scope of starting materials which can be now used.

The fluorinated aromatics of pyridines produced by the present invention can be employed as chemical intermediates having a variety of applications. For example, fluorobenzene and o-fluorotoluenes are used as intermediates in making tranquilizers, 2-fluoropyridine is used as an intermediate in making contraceptives, and other uses for these types of products include insecticides and the like.

DETAILED DESCRIPTION OF THE INVENTION

The generalized reaction for the present invention may be represented by the formula $$R-NH_2 + HF + NaNO_2 \xrightarrow[\text{Compounds}]{\text{Tertiary Amine}} R-N{=}N-F \xrightarrow{\Delta} R-F$$

where an aminobenzene or aminopyridine substrate ($R-NH_2$) in HF is reacted with diazotization agent, represented here as sodium nitrite, to produce the corresponding diazonium fluoride, which is decomposed, usually by heat, to make the desired fluorobenzene or fluoropyridine. The improvement of the present invention over that of the prior art is the introduction of tertiary amine compounds, described more fully below, in the solution of HF. Of course, the reaction may be conducted according to either the one or two step methods described above.

For the present invention, suitable substrates include aromatic primary amines and unsaturated heterocyclic primary amines having the formula (I) or (II), respectively (I)

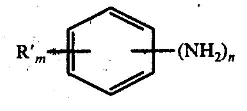

(II)

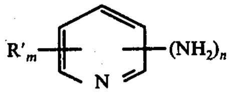

wherein R′ is a ring substituent selected from the group consisting of halogen, preferably chlorine, fluorine and bromine; alkyl, preferably lower alkyl having 1–4 carbon atoms; nitro; carboxyl; hydroxy; akoxy, preferably lower alkoxy having 1–4 carbon atoms; and/or a combination thereof; *m* is an integer having a value of 0–3 and *n* is an integer having a value of 1–2.

For purposes of further defining the present invention, the term "lower alkyl" shall, unless expressly stated to the contrary, means an alkyl having 1–4 carbon atoms including isopropyl and secondary butyl. Wherever the term "halogen" or "halo" is used herein, it shall be understood to include fluorine, chlorine, bromine and iodine unless it is expressly stated to the contrary.

Suitable aromatic substrates include, for example, o-, m- or p-toluidine, aniline, o-, m- or p-haloaniline, o-, m- or p-alkoxyaniline, o-, m- or p-aminophenol, o-, m- or p-nitroaniline and o-, m- or p-phenylene diamine. Likewise, illustrative compounds of the pyridine series include 2-, 3- or 4-aminopyridine, diaminopyridines such as 2,6-diaminopyridine, haloaminopyridines such as 2-amino-4-, 5- or 6-halopyridine and 3-amino-5- or 6-halopyridine, nitroaminopyridines such as 2-amino-4-, 5- or 6-methylpyridine and 2-amino-4,6-dimethylpyridine. The preferred substrates at the present time are o-toluidine and aniline because of their commercial applicability.

The usual diazotization agents, namely, sodium nitrite, potassium nitrite, nitrous anhydride, nitrous acid and nitrosyl halides or nitrosyl halide complexes with HF may be employed in the reaction and the nitrous acid may be prepared in-situ by known methods, for example, by dissolving an alkali metal nitrite in excess hydrogen fluoride. Where diazotization-fluorination of a single amino group is to be conducted, i.e., where n in formulae (I) or (II) has a value of 1, from about 1.0 to 1.5 moles of the diazotizing agent, preferably about 1.0 to 1.25, are employed per mole of substrate. Where tetrazotization, i.e., diazotization-fluorination of both amine groups of a diamine, is desired, i.e., *n* is 2, these amounts must be doubled to about 2.0 to 3.0 moles, preferably from about 2.0 to 2.5 moles of diazotizing agent per mole of substrate.

Hydrogen fluoride acts both as the source of fluorine for the reaction and as the medium for carrying out the reaction. Suitably, from about 2 moles up to about 30 moles of HF, preferably about 7.5 moles up to about 25 moles of HF, are employed per mole of substrate. Anhydrous HF is preferred but 70% aqueous up to anhydrous may be employed, if desired. The HF should be present in excess molar quantities over that necessary for the diazotization reaction because having too little of HF present will cause the reaction to run out of control and endanger the safety of the operation. On the other hand, having too much HF present lowers the economic value of the process. Anhydrous HF is favored because aqueous HF can cause corrosion to the equipment if not carefully controlled.

In accordance with the present invention, a solution of hydrogen fluoride containing selected tertiary amine compounds is utilized for both steps. As used herein, the term "tertiary amine compound" is used to encompass any compound within the six classes of compounds set forth below. This term is employed because the compounds herein have three carbon-nitrogen bonds (i.e., either single, double or triple) which commonly distinguish tertiary amines from primary and secondary amines. Of all the compounds listed below, the mixtures of 3- and 4-picoline or acetonitrile are preferred because of their relative low cost and their characteristics which lend themselves to being environmentally beneficial.

Exactly how the addition of tertiary amine compounds aids the diazotization-fluorination reaction has not been ascertained. It is believed that possibly a tertiary amine-hydrogen fluoride complex is formed in some cases and this complex is the particular means of getting the known beneficial results. It is thought that the free pair of electrons on the nitrogen of some amine compounds may attach one or more HF molecules and, thus, form a loose complex with them. However, some of the tertiary amine compounds cited below do not have this free pair of electrons (e.g., tertiary amine oxides) and thus it is not clear how they could form a complex. Furthermore, at this time, it is not known by the inventor how the above "complex", if formed, does exactly aid the diazotization and decomposition steps.

Tertiary amine compounds can be used in the HF solution provided they do not cause any appreciable hindrance or interference to the diazotization or decomposing steps or will not be susceptible to diazotization itself. Of all the specific examples of these compounds described below, none are known to the inventor to have these undesirable properites. And, preferably, it is desired that the tertiary amine compound be soluble in HF so that a homogeneous medium exists, and, therefore, a faster rate of reaction would result. But, heterogeneous solutions are also within the scope of the invention.

A large number of tertiary amine compounds exist which may be utilized and these may be divided into six different groups: unsaturated heterocyclic tertiary amines, aromatic tertiary amines, alkyl tertiary amines, saturated heterocyclic amines, nitriles and tertiary amine oxides. Of course, combinations of these compounds both within groups and between different groups can be also employed.

Group (I) of these compositions includes unsaturated heterocyclic tertiary amines having a nucleus of about 6–12 ring atoms, advantageously about 6–10, preferably 6, consisting of carbon and 1 or 2 atoms of nitrogen and substituted derivatives thereof having the formula $R_m$-X wherein X represents the heterocyclic nucleus described above, R is a carbon substituted substituent on the nucleus selected from the group consisting of lower alkyl, halogen, hydroxy loweralkyl, halo loweralkyl, lower alkoxy and

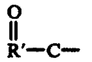

wherein R' is lower alkyl and wherein *m* is an integer having a value in the range of 0–3.

Thus, substituted or unsubstituted pyridine, quinoline, isoquinoline, pyrazine, indole, pyrrole and acridine may suitably be employed.

The preferred unsaturated heterocyclic tertiary amines are those having the formula:

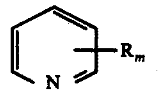

wherein $R_m$ is as defined above.

Illustrative compounds include the following:

Pyridine
α-, β- or γ-Picoline
Lutidines (Dimethylpyridine)
Collidines (Trimethylpyridines)
2-, 3- or 4-Ethylpyridine
5-Ethyl-2-Methylpyridine
2-Halopyridines
2-Ethanolpyridine
2-, 3- or 4-Acetylpyridine
Haloalkylpyridines
2-, 3- or 4-Methoxypyridine
2,6-Dimethoxypyridine
Quinoline
Isoquinoline
Lepidine (4-Methylquinoline)
Pyrazine
Acridine Group (II) includes aromatic tertiary amines having the formula:

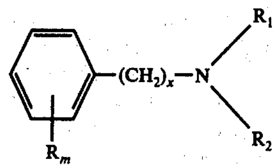

wherein $R_1$ and $R_2$ are each lower alkyl, hydroxy loweralkyl or phenyl, wherein $R_m$ is as defined above and wherein x is an integer having a value of 0–4, advantageously 0–2, preferably 0.

The preferred compounds of this group are thus disubstituted anilines having the formula:

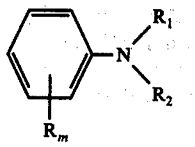

wherein $R_m$, $R_1$ and $R_2$ are as defined above. Illustrative compounds include N,N-dimethylaniline, N,N-diethylaniline, N-phenyldiethanolamine, N,N-phenyl-ethyl ethanolamine. Dialkylaminoalkylphenols such as dimethylaminomethylphenol are also advantageously employed.

Group (III) of tertiary amine compounds which has been found to be advantageously employed in accordance with the present invention includes alkyl tertiary amines and amides having the formula:

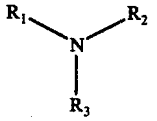

wherein each R is independently selected from the group consisting of alkyl having 1–12 carbon atoms and hydroxy loweralkyl and wherein one of said R groups may be

wherein R' is lower alkyl or hydrogen.

The preferred compounds of this group are the trialkylamines such as triethylamine, trinonylamine or dodecyldimethylamine but may also be a suitable lower alkanolamine such as triethanolamine, N-methyl diethanolamine or N,N-diethylethanolamine.

Preferred amide derivatives of this group of compounds are those in which R' has 1–2 carbon atoms, namely, dialkylformamides or acetamides such as dimethylformamide or dimethylacetamide.

Group (IV) includes the saturated heterocyclic tertiary amines having about 5–10, preferably about 5–8, nuclear atoms consisting of carbon and 1 or 2 nitrogen atoms. Preferably at least one of said nitrogen atoms is substituted with a lower alkyl or hydroxy loweralkyl group. Illustrative preferred compounds include N,N-dialkylpiperazines such as N,N-dimethylpiperazine, N-alkylpiperidines such as N-methylpiperidine, N-alkyldialkylpyrrolidines such as N-methyl 2,3-dimethylpyrrolidine, N-hydroxyalkylpiperidines such as N- methylhydroxyethylpiperidine, N-methyl-4-piperidone, 1,3-dimethylimidazolidine. Other compounds of this class include bicyclic tertiary amines such as quinuclidine and 1,4-diazo-bicyclo-(2,2,2)-octane.

Group (V) includes nitriles having the formula RC≡N wherein R is alkyl, preferably lower alkyl. The preferred is acetonitrile.

And, Group (VI) includes tertiary amine oxide having the formula:

$$R_1R_2R_3—N \rightarrow O$$

wherein $R_1$, $R_2$ and $R_3$ are alkyl groups, preferably a lower alkyl, hydroxy loweralkyl, phenyl or derivatives thereof. $R_1$, $R_2$ and $R_3$ can also represent the carbon portion of unsaturated heterocyclic ring having a nucleus of 6–12 ring atoms, advantageously 6–10, preferably 6 and substituted derivatives thereof. Illustrative examples of the group are triethylamine oxide, pyridine-N-oxide, 2-chloropyridine-N-oxide, picoline-N-oxide and 2,6-lutidine-N-oxide.

At least about 0.025 moles of the selected tertiary amine compound, advantageously about 0.025 to about 0.5, preferably about 0.05 to about 0.25 moles of the selected tertiary amine compound may be utilized per mole of hydrogen fluoride. Larger amounts may also be employed if desired but it is generally not economical to increase the amounts much above the limits specified. Lower amounts can also be used, but will result in reduced yields.

The diazotization-fluorination process may be conducted in at least two basic ways; as a single step diazotization-decomposition or as a two-step process in which diazotization is effected at low temperature and then the reaction mixture is heated to effect decomposition.

In the two step process the diazotization is conducted at a temperature in the range of about −20° to about 10° C, preferably about −10° to about 10° C, and this diazotization step is conducted in the usual manner by slowly adding the diazotization agent to a mixture of the substrate and the tertiary amine compound in HF. Alternatively, the first step may be started without the addition of the tertiary amine compound and then add this compound to the reaction mixture part way through the first step. Thereafter, the reaction mixture is heated to decomposition temperature which is the temperature at which nitrogen evolution becomes substantially complete. Generally, depending on which diazonium fluoride intermediate is being decomposed, this will occur by the time the temperature reaches the reflux temperature of the reaction mixture, namely, about 40°–50° C. In other instances, higher temperatures are required and usually these may be attained by heating under pressure or evaporating solvent until the desired temperature is reached. It should be noted that "decomposition" is defined herein as the removal of $N_2$ from the diazonium fluoride, preferably as shown by increased temperature. However, other methods, if applicable, could be used.

With some diazonium fluorides, however, notably certain o-substituted diazonium fluorides, tar formation may result if either of these techniques is employed. These may advantageously be decomposed by contacting the reaction mixture with a suitable heat exchange medium at a temperature above the distillation temperature of the resulting product as described in U.S. Pat. No. 3,950,444, for example, 100°–350° C.

If it is desired to conduct the reaction in a single step, the diazotization agent is dissolved in one portion of the HF, the substrate in another with HF containing the tertiary amine compounds added to one or both. The diazotization agent in HF is then added slowly to the substrate in HF at a temperature above the decomposition temperature of the diazonium fluoride. Suitable temperatures for the one-step reaction thus fall within the range from about 15° to about 50° C, that is from as low as the temperature at which decomposition begins to the reflux temperature of the reaction mixture. If that is not sufficiently high, then the reaction can be conducted under pressure to attain higher temperatures.

It is apparent from the foregoing discussion that depending on the technique for conducting the reaction and on the particular substrate that diazotization temperatures may vary within the range of −20° C up to about 50° C and that decomposition temperatures may vary in the range of about 15° up to about 350° C, preferably 15° up to about 100° C.

It is also apparent that it is preferable to operate at atmospheric pressure but that lower or higher pressures may be used as desired for most substrates, for example, 0.5 to 50 atmospheres, advantageously 0.8 to about 1.5 atmospheres.

Where either a one or two-step process is employed, the decomposition time will vary with the speed at which the diazotization agent is added and/or with the temperature. Where a heat exchange medium is used, the decomposition is instantaneous, where a two-step process is utilized, the decomposition time will depend on the speed at which temperature is increased and, in the one-step process, on the speed at which the diazotization agent is added to the substrate/HF mixture. Decomposition time may thus vary from about 0.5 seconds up to about 25 hours.

The present process can be carried out in any conventional chemical reactor which is suitable for this purpose. The reactor can be made out of stainless steel or plastics such as chlorotrifluoroethylene or tetrafluoroethylene polymers. The preferred is a conventional type 304 stainless steel reactor.

The following examples further illustrate the invention. All percentages are by weight unless expressly stated to the contrary.

EXAMPLE 1 m-Fluoroaniline in HF/Pyridine

To a 1-liter stainless steel reactor (ss 304) cooled at −10° C was charged anhydrous hydrogen fluoride (400 g; 20 moles). Pyridine (120.0 g; 1.52 moles) was added over 0.25 hour, followed by the addition of m-fluoroaniline (111.1 g; 1.0 mole). Diazotization was accomplished by the addition of sodium nitrite (84 g; 1.2 moles) at 0° ± 5° C during a 2 hour period.

m-Fluorophenyl diazonium fluoride was then decomposed at 34°–64° C during a 5.5 hour period. During the decomposition, nitrogen saturated with hydrogen fluoride was vented through the refrigerated condensers. The hydrogen fluoride refluxed back to the reaction vessel.

After the decomposition was complete (no gas evolution), the reaction mixture was cooled to 0° C and transferred to a neutralization vessel containing ammonium hydroxide (29%). m-Difluorobenzene was then recovered from the basic mixture by steam distillation to give a colorless liquid (105 g) (which assayed 76.4% m-difluorobenzene and 23.6% pyridine by vapor phase chromatography: 10′ × ¼ Al 10% Carbowax 20M)

(70.3% analytical yield). Product purification can be effected by extraction of pyridine with hydrochloric acid to give m-difluorobenzene in 99.9% purity (VPC).

The remaining pyridine in the steam distillation vessel can be removed by further distillation and processed for recycle.

This example demonstrates that superior results are obtained when a complexing agent of Group (I) is used in the HF medium.

EXAMPLE 2 m-Fluoroaniline in HF/Triethylamine

A 1-liter stainless steel reactor (ss 304) cooled at −10° C was charged with anhydrous HF (400 g; 20 moles). Then, triethylamine (153.8 g; 1.52 moles) was added (0.5 hours), followed by the addition of m-fluoroaniline (111.1 g; 1.0 mole). Diazotization was accomplished by the addition of $NaNO_2$ (84 g; 1.2 moles) at 0°± 5° C.

m- Fluorophenyl diazonium fluoride was then decomposed at 46°–65° C during a 7-hour period. After the decomposition was complete (not gas evolution), the mixture was cooled to 0° C and transferred to a neutralization vessel containing 29% ammonium hydroxide. m-Difluorobenzene was then recovered from the basic mixture by steam distillation to give a liquid (wt. 255.3 g) (which assayed 29.6% m-difluorobenzene and 53.6% triethylamine by vapor phase chromatography: 5′ × 174 inches ss 20% SF 96 column) (63.2% analytical yield).

This example shows that superior results are obtained when a complexing agent of Group (III) is used in HF solution.

EXAMPLE 3 m-Fluoroaniline in H//DMSO

To a 1-liter stainless steel (ss 304) reactor cooled at −10° C. was charged anhydrous HF (400 g; 20 moles). Then, m-fluoraniline (1.0 mole; 111.1 g) and dimethyl sulfoxide (5.45 moles; 435 g) were successively added. Diazotization was accomplished by addition of $NaNO_2$ (84 g: 1.2 moles) at 0° ± 5° C.

M-Fluorophenyl diazonium fluoride was then decomposed at 50°–76° C during a 4-hour period. After the decomposition was complete (not gas evolution), the mixture was cooled to 0° C and transferred to a neutraliztion vessel containing 29% ammonium hydroxide. m-Difluorobenzene was steam distilled from the basic mixture to give a liquid, wt. 83.9 g, which assayed 98.9% m-difluorobenzene by vapor phase chromatography (10% Carbowx 20N) (7.28% yield). The reactor was severely pitted and had suffered at 2.7 wt. % loss.

This example shows the prior art teaching of using DMSO in the HF medium. Although such use leads to relatively high yields, the damage to equipment through corrosion was extensive.

EXAMPLE 4 m-Fluoroaniline in HF Alone

To a 1-liter stainless steel reactor (ss 304) cooled at −10° C was charged anhydrous hydrogen fluoride (400 g; 20 moles). Then, m-fluoroaniline (111.1 g; 1.0 mole) was added during a 0.25-hour period, followed by the addition of sodium nitrite (84 g; 1.2 moles) at 0° C ± 5° C.

m-Fluorophenyldiazonium fluoride was then decomposed at 38°–55° C during a 9.5-hour period.

After the decomposition was complete (no gas evolution), the reaction mixture was cooled to 0° C and transferred to a neutralization vessel containing ammonium hydroxide (29%). m-Difluorobenzene was isolated in only 2.8% yield; the steam distillation liquid contained appreciable tars (268.7 g).

This example teaches that without complexing in the HF medium agent, the yield of making m-difluorobenzene is very low. Comparison of Examples 1 through 4 show that superior results are obtained with aminobenzene substrates when the present invention is employed.

EXAMPLE 5 o-Toluidine in HF/Pyridine

To a 1-liter ss 304 reactor cooled at −10° C was charged anhydrous HF (400 g; 20 moles). Then, pyridine (120.0 g; 1.52 moles) was added, followed by the addition of o-toluidine (107.2 g; 1.0 mole). Diazotization was accomplished by the addition of sodium nitrite (75.9 g; 1.1 moles) at 0° ± 5° C during a 1.5-hour period.

o-Tolydiazonium fluoride was then decomposed at 17°–55° C during a 4.5-hour period. During the decomposition, nitrogen saturated with HF was vented through the refrigerated condensers. The hydrogen fluoride refluxed back to the reaction vessel.

After the decomposition was complete (no gas evolution), the reaction mixture was cooled to 0° C and transferred to a Teflon separatory funnel. Facile phase separation of the organic (wt. 97.0 g) and hydrogen fluoride (wt. 580.2 g) layers was noted.

The organic layer was neutralized by addition to 500 ml of 10% sodium hydroxide and steam distilled to give 85.6 g of organic, (VPC: 10% Carbowax 20M), 98.6% assay (0.767 mole).

The HF layer was then transferred to a neutralization vessel containing ammonium hydroxide at 0° C. The neutralized solution (pH∼9) was steam distilled to give an organic layer (wt. 8.1 g) which assayed by VPC, o-fluorotoluene (60.9%, 0.045 mole; 4.5% yield) and pyridine (38.3%; 3.1 g; 0.039 mole). Further distillation of the steam distillation liquor provided 582.0 g which assayed (by titration), 19.96% pyridine (116.1 g or 1.47 mole).

The combined yield of o-fluorotoluene from processing of both HF and organic phases was 81.2%; recovery of pyridine was 99.3%.

This example teaches that superior results are obtained when a complexing agent of Group (I) is used in the HF medium.

EXAMPLE 6 o-Tuluidine in HF/3- and 4-Picolines (Two-Step)

To a 1-liter ss 304 reactor cooled at −10° C was successively charged anhydrous HF (400 g; 20 moles), a mixture of 3- and 4-picoline (15:85 ratio) (69.8 g; 0.75 mole) and o-toluidine (107.2 g; 1.0 mole) at −10° C. Diazotization was effected by addition of $NaNO_2$ (75.9 g; 1.1 moles) at 0° + 5° C.

o-Tolyldiazonium fluoride was then decomposed at 13°–43° C during a 4.5-hour period. The cooled (0°C) fluorination mixture was transferred to a Teflon separatory funnel. Phasing provided an organic (wt. 98.2 g) and a lower HF (wt. 542.8 g) layer.

Neutralization of the organic layer with ∼10% NaOH, followed by steam distillation gave 84.9 g of organic (VPC: 99.6%; wt. 84.6 g; 0.771 mole).

Processing of the HF layer by addition to ammonium hydroxide, followed by steam distillation gave 9.9 g of an organic (VPV: 34.4% o-fluorotoluene; 3.1 g; 0.029 mole). Continued steam distillation resulted in quantitative recovery of the mixed picolines (0.756 mole by potentiometric titration with correction for ammonia).

The combined yield of o-fluorotoluene from processing of the HF and organic layers was 80.0%.

This is another example of superior results being obtained when a complexing agent of Group (I) is used.

EXAMPLE 7 o-Toluidine in HF/3- and 4-Picolines (One-Step)

To a 1-liter ss 304 reactor cooled at 10° C was charged anhydrous HF (240 g; 12 moles), followed by addition of $NaNO_2$ (75.9 g; 1.1 moles) at 0° ± 5° C (2-hour period). The solution of HONO/HF was stored at 0° C prior to addition to the substrate.

To a 2-liter ss 304 reactor cooled at −10° C was charged anhydrous HF (160 g; 8 moles), followed by successive addition of the 3- and 4-picolines (60.8 g; 0.75 mole) and o-toluidine (107.2 g; 1.0 mole). This solution of o-toluidine hydrofluoride was then heated to 25°-30° C and the liquid HONO/HF added sub-surface during a 1.5 hour period. The reaction mixture was then heated at 35°-45° C for 0.75 hour.

The cooled (0° C) fluorination mixture was transferred to a Teflon separatory funnel. Phasing provided an organic (wt. 124.9 g) and a lower HF (446.7 g) layer. Neutralization of the organic layer with ~10% NaOH, followed by steam distillation gave 89.5 g of organic (VPC: 91.1%; 81.4 g; 0.739; balance was primarily picolines, 7.4%).

Processing of the HF layer by addition to ammonium hydroxide, followed by steam distillation gave 5.2 g of o-fluorotoluene (0.047 mole).

The combined yield of o-fluorotoluene from processing of the HF and organic layer was 78.6%.

Again, superior results when using a complexing agent of Group I in the HF medium.

EXAMPLE 8 o-Toluidine in HF/Dialkylpyridine

To a 1-liter ss 304 reactor cooled at −10° C was successively charged anhydrous HF (400 g; 20 moles), a mixture was 2-methyl-5-ethylpyridine and 2-methyl-3-ethylpyridine ("LAP"-Reilly Tar; 90.9 g; 0.75 mole) and o-toluidine (107.2 g; 1.0 mole) at −10° C. Diazotization was accomplished by addition of $NaNO_2$ (75.9 g; 1.1 moles) at 0° ±5° C. o-Tolyldiazonoium fluoride was then decomposed at 12°-45° C during a 4.5 hour period. The cooled (0° C) fluorination mixture was transferred to a Teflon separatory funnel. Phasing provided an organic (wt. 112 g) and a lower HF (wt. 525.6 g) layer.

The organic layer was neutralized by addition to 500 ml of ~10% NaOH and steam distilled to give 81.1 g organic (VPC: o-fluorotoleuene, 95.9%, 77.7 g; 0.706 mole).

Processing of the HF layer by addition to ammonium hydroxide, followed by steam distillation gave 74.6 g of an organic (o-fluorotoluene content, 12.4%; 9.2 g; 0.084 mole).

The combined yield of o-fluorotoluene from processing of both HF and organic layers was 79.0%.

Another example of a complexing agent of Group I being used in the HF medium to obtain superior results.

EXAMPLE 9 o-Toluidine in HF/N,N-dimethylaniline

To a 1-liter ss 304 reactor cooled at −10° C was successively charged anhydrous HF (400 g; 20 moles), N,N-dimethylaniline (0.75 mole; 90.0 g) and o-toluidine (1.0 mole; 107.2 g) at −10° C. Diazotization was effected by addition of $NaNO_2$ (95.0 g; 1.37 moles) at 0° ± 5° C.

o-Tolyldiazonium fluoride was then decomposed at 29° -45° C. during a 5 hour period. The cooled (0° C) reaction mixture was transferred to a Teflon separatory funnel. Phasing provided an organic (wt. 93.0 g) and a lower HF (wt. 572.0 g) layer.

The organic layer was neutralized by addition to 500 ml of ~10% NaOH and steam distilled to give 82.5 g organic (VPC: 98.9% o-fluorotoluene; 81.5 g; 0.741 mole).

The HF layer was neutralized by addition to ammonium hydroxide at 0° C and steam distilled to give two organic fractions:

(I) wt. 7.7 g: o-fluorotoluene, 41.9%; 3.2 g; 0.029 mole
(II) wt. 34.4 g: o-fluorotoluene, 6.6%; 2.3 g; 0.021 mole The combined yield of o-fluorotoluene from processing of both HF and organic layers was 79.1%.

This example demonstrates that superior results are obtained when a complexing agent of Group II is used in the HF medium.

EXAMPLE 10 o-Toluidine in HF/Trimethylamine

To a 1-liter ss 304 reactor cooled to −10° C was successively charged anhydrous HF (400 g; 20 moles), trimethylamine (43.4 g; 0.73 mole) and o-toluudine (107.2 g; 1.0 mole) at −10° C. Diazotization was accomplished by addition of $NaNO_2$ (75.9 g; 1.1 moles) at 0° ± 5° C.

o-Tolyldiazonium fluoride was then decomposed at 23° - 41° C during a 5 hour period. The cooled (0° C) fluorination mixture was then transferred to a Teflon separatory funnel. Phasing provided an organic (wt. 122.1 g) and a lower HF (wt. 452.7 g) layer.

The organic layer was neutralized by addition to 500 ml of ~10% sodium hydroxide and steam distilled to give 89.2 g organic (VPC: o-fluorotoluene, 98.7%; 89.2 g; 0.810 mole).

Neutralization of the HF layer at 0° C. with ammonium hydroxide followed by steam distillation gave o-fluorotoluene (1.85 g; 0.017 mole).

The combined yield of o-fluorotoluene from processing of both HF and organic layers was 82.7%.

This example shows that superior results are obtained when a complexing agent of Group III is used.

EXAMPLE 11 o-Toluidine in HF/Acetonitrile

To a 1-liter ss 304 reactor cooled at −10° C was successively charged anhydrous HF (400 g; 20 moles), acetonitrile (71.7 g; 1.75 moles) and o-toluidine (107.2 g; 1.0 mole) at −10° C. Diazotization was accomplished by addition of $NaNO_2$ (75.9 g; 1.1 moles) at 0° ± 5° C.

o-Tolyldiazonium fluoride was then decomposed at 10° - 48° C during a 5.5 hour period. The cooled (0° C) fluorination mixture was transferred to a Teflon separatory funnel. Phasing provided an organic (wt. 144.7 g) and a lower HF (wt. 503.7 g) layer.

The organic layer was neutralized by addition to 500 ml of ~10% NaOH and steam distilled to give 83.0 g organic (VPC column: 20% SF-96), (o-fluorotoluene, 98.9% assay; 82.1 g; 0.745 mole).

Processing of the HF layer provided and additional quantity of o-fluorotoluene (6.2 g; 0.057 mole).

The combined yield of o-fluorotoluene from processing of both HF and organic layers was 80.3%.

Superior results are again shown when a complexing agent of Group V is employed in the HF medium.

EXAMPLE 12 o-Toluidine in HF/N,N-Dimethylformamide

To a 1-liter ss 304 reactor cooled at −10° C was successively charged anhydrous HF (400 g; 20 moles), N,N-dimethylformamide (54.8 g; 0.75 mole) and o-toluidine (107.2 g; 1.0 mole) at −10° C. Diazotization was accomplished by addition of $NaNO_2$ (75.9 g; 1.1 moles) at 0° ± 5° C.

o-Tolyldiazonium fluoride was then decomposed at 12° - 45° C during a 5 hour period. The cooled 0° C fluorination mixture was transferred to a Teflon separatory funnel. Phasing provided an organic (wt. 101.7 g) and an lower HF (wt. 513.6 g) layer.

The organic layer was neutralized by addition to 500 ml of ~10% NaOH and steam distilled to give 77.2 g organic (VPC: o-fluorotoluene, 99.3%; 76.6 g; 0.696 mole).

Processing of the HF layer by addition to ammonium hydroxide, followed by steam distillation provided 3.9 g of organic (o-fluorotoluene content, 81.1%, 3.1 g; 0.029 mole).

The combined yield of o-fluorotoluene from processing of both HF and organic layers was 72.5%.

This example shows that an amide complexing agent of Group III gets superior results when used in HF medium.

EXAMPLE 13 o-Toluidine in HF/N-Methyl-2-Pyrrolidone

To a 1-liter ss 304 reactor cooled at −10° C was successively charged anhydrous HF (400 g; 20 moles), N-methyl-2-pyrrolidone (74.3 g; 0.75 mole) and o-toluidine (107.2 g; 1.0 mole) at −10° C. Diazotization was accomplished by addition of $NaNO_2$ (75.9 g; 1.1 moles) at 0° ± 5° C.

o-Tolyldiazonium fluoride was then decomposed at 13° - 46° C during a 4.5 hour period. The cooled 0° C fluorination mixture was transferred to a Teflon separatory funnel. Phasing provided an organic (wt. 123 g) and a lower HF (wt. 523.5 g) layer.

The organic layer was neutralized by addition to 500 ml of ~10% NaOH and steam distilled to give 77.5 g organic (VPC: o-fluorotoluene, 99.5%, 76.8 g; 0.698 mole).

Processing of the HF layer by addition to ammonium hydroxide, followed by steam distilled gave 7.6 g of organic (VPC: 81.9% o-fluorotoluene; 6.2 g; 0.056 mole).

The combined yield of o-fluorotoluene from processing of both HF and organic layers was 75%.

This example demonstrates the superior results obtained when employing a complexing agent of Group IV.

EXAMPLE 14 o-Toluidine in HF Alone

In several runs a 1-liter ss 304 reactor cooled at −10° C was successively charged anhydrous HF (400 g; 20 moles) and o-toluidine (107.2 g; 1.0 mole). Diazotization was accomplished by addition of $NaNO_2$ at 0° C ± 5° C.

o-Tolyldiazonium fluoride was then decomposed at 13° - 45° C over a 4.5 hour period. It was noted that phasing of organic and inorganic layers was poor. Yields of the several runs were as follows:

| Run | Yield | Work-Up |
|---|---|---|
| 1 | 64 % | Organic layer only processed. |
| 2 | 64 % | Direct neutralization of combined layers. |
| 3 | 65.5% | Pressure fluorination. Direct neutralization of both layers. |
| 4 | 68 % | Both layers processed separately. |
| 5 | 64 % | Dilution with water, phasing then work-up. |

This example demonstrates the consistently low yields obtained when HF alone is used as the diazotization-fluorination medium. By contrast, the use of a tertiary amine compound in Examples 5-13 and 15 equally and consistently produced substantially improved yields with aminobenzenes in making the corresponding fluoroaromatics.

EXAMPLE 15 o-Toluidine in HF/Pyridine-N-Oxide

To a 2-liter ss 304 reactor cooled at −10° C is charged anhydrous hydrogen fluoride (400 g; 20 moles). Then, pyridine N-oxide (0.75 mole; 71.3 g) and o-toluidine (107.2 g; 1.0 mole) are successively added. Diazotization was accomplished by the addition of sodium nitrite (75.9 g; 1.1 moles) at 0° ± 5° C during a 2.5 hour period.

o-Tolydiazonium fluoride was then decomposed at 16-49° C during a 5.5 hour period. During the decomposition, nitrogen saturated with HF is vented through the refrigerated condenser. The hydrogen fluoride refluxes back to the reaction vessel.

After the decomposition is complete, (no gas evolution) the reaction mixture is cooled to 0° C and transferred to a Teflon separatory funnel. Facile phase separation of the organic and hydrogen fluoride layers was noted.

The organic layer was neutralized by addition to 600 ml of 10% sodium hydroxide and steam-distilled to give 85.8 g organic VPC (20% QF-1 column), 99.4% o-fluorotoluene assay (0.773 mole).

The HF layer was then transferred to a neutralization vessel containing ammonium hydroxide at 0° C. The neutralized solution (pH ~9) was steam-distilled to give an organic layer (wt. 1.8 g) which assayed by VPC, 91.4% o-fluorotoluene (1.65 g; 0.014 mole).

The combined yield of o-fluorotoluene from processing of both organic and hydrogen fluoride phases was 78.7%.

This example demonstrates that superior results can be obtained by employing a complexing agent of Group VI in the medium of HF.

What is claimed is:

1. In a process for preparing a fluorobenzene or a fluoropyridine by (1) diazotizing a corresponding aminobenzene or aminopyridine substrate in the presence of hydrogen fluoride and a diazotization agent selected from the group consisting of sodium nitrite, potassium nitrite, nitrous anhydride, nitrous acid, a nitrosyl halide, and a complex of a nitrosyl halide with hydrogen fluoride to produce a corresponding diazonium fluoride and (2) decomposing said diazonium fluoride; wherein said aminobenzene and aminopyridine substrates have either formula (I) or (II):

(I)

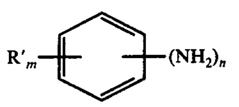

(II)

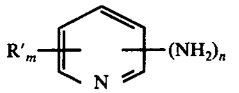

wherein R′ is a ring substituent selected from the group consisting of halogen; alkyl; nitro; carboxyl; hydroxy; alkoxy; and combinations thereof; m is an integer having a value of 0–3; and *n* is an integer having a value of 1–2, the improvement which comprises:

conducting said diazotization and decomposition steps in a solution of hydrogen fluoride containing tertiary amine compounds selected from the group consisting of unsaturated heterocyclic tertiary amines, aromatic tertiary amines, alkyl tertiary amines, saturated heterocyclic amines, nitriles, tertiary amine oxides and combinations thereof.

2. The process of claim 1 wherein said tertiary amine compound is an unsaturated heterocyclic tertiary amine having a nucleus of 6–10 ring atoms consisting of carbon and 1 or 2 atoms of nitrogen and substituted derivatives thereof having the formula $R_m$-X wherein X represents said nucleus, wherein R is a carbon substituted substituent on said nucleus selected from the group consisting of lower alkyl, halogen, hydroxy loweralkyl, halo loweralkyl, lower alkoxy and

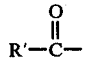

wherein R′ is lower alkyl, and wherein m is an integer having a value of 0–3.

3. The process of claim 2 wherein said tertiary amine has the formula:

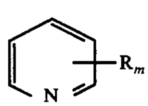

wherein each R is a carbon substituted substituent selected from the group consisting of lower alkyl, halogen, hydroxy loweralkyl, halo loweralkyl, lower alkoxy and

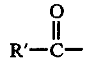

wherein R′ is lower alkyl and wherein m is an integer having a value of 0–3.

4. The process of claim 3 wherein said tertiary amine is pyridine.

5. The process of claim 2 wherein said nucleus is selected from the group consisting of 3-picoline, 4-picoline, quinoline, isoquinoline, pyrazine, indole, pyrrole and acridine.

6. In a process for preparing a fluorobenzene or a fluoropyridine by (1) diazotizing a corresponding aminobenzene or aminopyridine substrate in the presence of hydrogen fluoride and a diazotization agent selected from the group consisting of sodium nitrite, potassium nitrite, nitrous anhydride, nitrous acid, a nitrosyl halide, and a complex of a nitrosyl halide with hydrogen fluoride, to produce a corresponding diazonium fluoride and (2) decomposing said diazonium fluoride; wherein said aminobenzene and aminopyridine substrates have either formula (I) or (II):

(I)

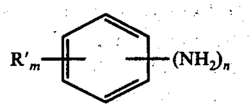

(II)

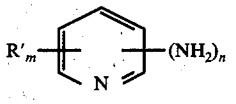

wherein R′ is a ring substituent selected from the group consisting of halogen; alkyl; nitro; carboxyl; hydroxy; alkoxy; and combinations therefor; m is an integer having a value of 0–3; and *n* is an integer having a value of 1–2, the improvement which comprises:

conducting said diazotization and decomposition steps in a solution of hydrogen fluoride containing tertiary amine compounds selected from the group consisting of aromatic tertiary amines, alkyl tertiary amines, saturated heterocyclic amines, nitriles, tertiary amine oxides and combinations thereof.

7. The process of claim 6 wherein said tertiary amine is an aromatic tertiary amine having the formula:

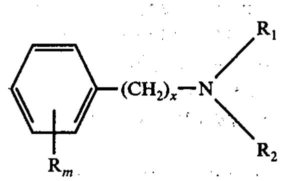

wherein $R_1$ and $R_2$ are each selected from the group consisting of lower alkyl, hydroxy loweralkyl and phenyl, wherein R is selected from the group consisting of lower alkyl, halogen, hydroxy loweralkyl, halo loweralkyl, lower alkoxy and

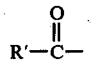

wherein R′ is lower alkyl, wherein *m* is an integer having a value in the range of 0–3 and wherein *x* is an integer having a value of 0–4.

8. The process of claim 7 wherein said tertiary amine is an N,N-disubstituted aniline having the formula:

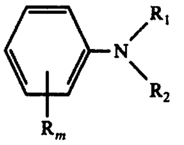

wherein $R_m$, $R_1$ and $R_2$ are as defined in claim 7.

9. The process of claim 6 wherein said tertiary amine is an alkyl tertiary amine or amide having the formula:

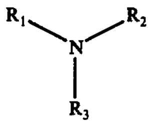

wherein each R is independently selected from the group consisting of alkyl having 1-12 carbon atoms and hydroxy loweralkyl and wherein one of said R groups may be

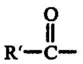

wherein R' is lower alkyl or hydrogen.

10. The process of claim 9 wherein said tertiary amine is a trialkylamine.

11. The process of claim 6 wherein said tertiary amine is a saturated heterocyclic amine having about 5-10 nuclear carbon atoms consisting of carbon and 1 or 2 nitrogen atoms.

12. The process of claim 11 wherein at least one of said nitrogen atoms is substituted with a substituent selected from the group consisting of lower alkyl and hydroxy loweralkyl.

13. The process of claim 12 wherein said tertiary amine is N-methyl-2-pyrrolidone.

14. The process of claim 6 wherein said tertiary amine is a nitrile having the formula RC≡N wherein R is an alkyl.

15. The process of claim 14 wherein said nitrile is acetonitrile.

16. The process of claim 6 wherein said tertiary amine compound is a tertiary amine oxide having the formula:

$$R_1R_2R_3—N \rightarrow O$$

wherein $R_1$, $R_2$ and $R_3$ are independently selected from the group consisting of alkyl, hydroxy loweralkyl, phenyl, the carbon portion of an unsaturated heterocyclic ring having a nucleus of about 6-12 ring atoms and substituted derivatives thereof.

17. The process of claim 16 wherein said tertiary amine oxide is pyridine-N-oxide.

18. The process of claim 6 wherein said tertiary amine compounds are employed in amounts ranging from about 0.025 to about 0.5 moles per mole of hydrogen fluoride.

19. The process of claim 18 wherein said solution of hydrogen fluoride is present in a range from about 2 moles to about 30 moles per mole of said aminobenzene or aminopyridine substrate.

20. The process of claim 19 wherein said diazotization and said decomposition steps are carried out in separate steps.

21. The process of claim 19 wherein said diazotization and said decomposition steps occur simultaneously.

22. The process of claim 19 wherein said diazotization and decomposition steps are conducted in a solution of hydrogen fluoride containing from about 0.05 to about 0.25 moles of tertiary amine ion per mole of hydrogen fluoride, and from about 7.5 to about 25 moles of hydrogen fluoride are present per one mole of said aminobenzene or aminopyridine present.

23. The process of claim 22 wherein o-fluorotoluene is produced by diazotizing o-toluidine with sodium nitrite and anhydrous hydrogen fluoride.

24. The process of claim 23 wherein said diazotization and decomposition steps occur in separate steps.

* * * * *